(12) United States Patent
Koh et al.

(10) Patent No.: US 10,745,472 B2
(45) Date of Patent: Aug. 18, 2020

(54) COMPOSITION FOR PREVENTING AND TREATING EYE DISEASES INCLUDING ANTI-ANG2 ANTIBODY

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Gou Young Koh, Daejeon (KR); Jaeryung Kim, Daejeon (KR); Do Young Park, Daejeon (KR)

(73) Assignees: INSTITUTE FOR BASIC SCIENCE, Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/473,685

(22) PCT Filed: Dec. 19, 2017

(86) PCT No.: PCT/KR2017/014981
§ 371 (c)(1),
(2) Date: Jun. 26, 2019

(87) PCT Pub. No.: WO2018/124582
PCT Pub. Date: Jul. 5, 2018

(65) Prior Publication Data
US 2019/0330324 A1    Oct. 31, 2019

(30) Foreign Application Priority Data

Dec. 26, 2016 (KR) .................. 10-2016-0179099
Dec. 18, 2017 (KR) .................. 10-2017-0174201

(51) Int. Cl.
| *A61K 39/395* | (2006.01) |
| *A61K 39/00* | (2006.01) |
| *C07K 16/22* | (2006.01) |
| *A61P 27/02* | (2006.01) |
| *A61P 27/06* | (2006.01) |

(52) U.S. Cl.
CPC ............ *C07K 16/22* (2013.01); *A61P 27/02* (2018.01); *A61P 27/06* (2018.01); *A61K 2039/505* (2013.01); *C07K 2317/565* (2013.01)

(58) Field of Classification Search
None
See application file for complete search history.

(56) References Cited

U.S. PATENT DOCUMENTS

| 2003/0040463 | A1* | 2/2003 | Wiegand | A01K 67/0275 514/1 |
| 2011/0150895 | A1* | 6/2011 | Ryu | C07K 16/22 424/145.1 |
| 2013/0259859 | A1* | 10/2013 | Ott | A61K 45/06 424/133.1 |
| 2014/0065151 | A1* | 3/2014 | Brinkmann | C07K 16/22 424/139.1 |
| 2015/0030603 | A1 | 1/2015 | Kim et al. | |
| 2016/0053025 | A1* | 2/2016 | Oh | C07K 16/22 424/136.1 |
| 2017/0183401 | A1* | 6/2017 | Jo | C07K 16/22 |

FOREIGN PATENT DOCUMENTS

| KR | 10-2015-0014077 | 2/2015 |
| KR | 10-2015-0028087 | 3/2015 |
| KR | 10-2015-0032075 | 3/2015 |
| KR | 10-2015-0136031 | 12/2015 |
| WO | 2016/061551 | 4/2016 |

OTHER PUBLICATIONS

Rennel, E. S. et al., "A Human Neutralizing Antibody Specific to Ang-2 Inhibits Ocular Angiogenesis", Microcirculation, 2011, vol. 18, pp. 598-607.
Hammes, H.-P. et al., "Angiopoietin-2 Causes Pericyte Dropout in the Normal Retina", Diabetes, 2004, vol. 53, pp. 1104-1110.
NCBI Accession No. O15123, "RecName: Full=Angiopoietin-2; Short=ANG-2; Flags: Precursor", UniProtKB/Swiss-Prot: O15123. 1, Feb. 13, 2019.
NCBI Accession No. Q8MIK6, "Angiopoietin 2", UniProtKB/Swiss-Prot: Q8MIK6, Oct. 31, 2006.
NCBI Accession No. O35608, "RecName: Full=Angiopoietin-2; Short=ANG-2; Flags: Precursor", UniProtKB/Swiss-Prot: O35608. 2, Feb. 13, 2019.
NCBI Accession No. O35462, "RecName: Full=Angiopoietin-2; Short=ANG-2; Flags: Precursor", UniProtKB/Swiss-Prot: O35462. 2, Jan. 16, 2019.
KIPO, Office Action of KR 10-2017-0174201 dated Jan. 15, 2019.

* cited by examiner

*Primary Examiner* — Maher M Haddad
(74) *Attorney, Agent, or Firm* — Lex IP Meister, PLLC

(57) ABSTRACT

The present invention relates to a composition which is for preventing and treating eye diseases and comprises an anti-angiopoietin-2 (Ang2) antibody and, more specifically, to a novel use of an anti-Ang2 antibody as an agent for preventing or treating eye diseases, wherein the anti-Ang2 antibody is specifically coupled to Ang2, is coupled to a Tie2 receptor together with Ang2, and has improved affinity. The composition according to the present invention can be usefully used to develop a treatment agent for macular degeneration, diabetic retinopathy, and glaucoma.

2 Claims, 6 Drawing Sheets
Specification includes a Sequence Listing.

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: CDRH1

<400> SEQUENCE: 1

Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: CDRH2

<400> SEQUENCE: 2

Lys Ile Ser Tyr Ser Gly Lys Thr Asp Tyr Asn Pro Ser Leu Lys Ser
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: CDRH3
```

```
<400> SEQUENCE: 3

Gly Asn Phe Glu Gly Ala Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: CDRL1

<400> SEQUENCE: 4

Lys Ala Ser Gln Ser Val Ser Asn Asp Val His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2

<400> SEQUENCE: 5

Tyr Ala Ser Ile Pro Tyr Pro
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3

<400> SEQUENCE: 6

Gln Gln Asp Tyr Ser Ser Pro Trp Thr
1               5

<210> SEQ ID NO 7
<211> LENGTH: 118
<212> TYPE: PRT
<213> ORGANISM: Artificial Sequence
<220> FEATURE:
<223> OTHER INFORMATION: VH

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Lys Ile Ser Tyr Ser Gly Lys Thr Asp Tyr Asn Pro Ser Leu
    50                  55                  60

Lys Ser Arg Ser Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Phe Glu Gly Ala Met Asp Tyr Trp Gly Gln Gly Thr
            100                 105                 110

Leu Val Thr Val Ser Ser
        115
```

```
<210> SEQ ID NO 8
<211> LENGTH: 107
<212> TYPE: PRT
<213> ORGANISM: Artificial Sequence
<220> FEATURE:
<223> OTHER INFORMATION: VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val His Trp Tyr Gln Gln Lys Pro Gly Lys Ala Pro Lys Leu Leu Ile
        35                  40                  45

Tyr Tyr Ala Ser Ile Pro Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 9
<211> LENGTH: 496
<212> TYPE: PRT
<213> ORGANISM: Artificial Sequence
<220> FEATURE:
<223> OTHER INFORMATION: Ang2

<400> SEQUENCE: 9

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205
```

```
Ile Lys Glu Glu Lys Asp Gln Leu Gln Val Leu Val Ser Lys Gln Asn
    210             215                 220

Ser Ile Ile Glu Glu Leu Glu Lys Lys Ile Val Thr Ala Thr Val Asn
225             230              235                 240

Asn Ser Val Leu Gln Lys Gln Gln His Asp Leu Met Glu Thr Val Asn
            245             250                 255

Asn Leu Leu Thr Met Met Ser Thr Ser Asn Ser Ala Lys Asp Pro Thr
            260             265             270

Val Ala Lys Glu Glu Gln Ile Ser Phe Arg Asp Cys Ala Glu Val Phe
        275             280              285

Lys Ser Gly His Thr Thr Asn Gly Ile Tyr Thr Leu Thr Phe Pro Asn
    290             295              300

Ser Thr Glu Glu Ile Lys Ala Tyr Cys Asp Met Glu Ala Gly Gly Gly
305             310              315                 320

Gly Trp Thr Ile Ile Gln Arg Arg Glu Asp Gly Ser Val Asp Phe Gln
            325             330              335

Arg Thr Trp Lys Glu Tyr Lys Val Gly Phe Gly Asn Pro Ser Gly Glu
            340             345              350

Tyr Trp Leu Gly Asn Glu Phe Val Ser Gln Leu Thr Asn Gln Gln Arg
        355             360              365

Tyr Val Leu Lys Ile His Leu Lys Asp Trp Glu Gly Asn Glu Ala Tyr
    370             375              380

Ser Leu Tyr Glu His Phe Tyr Leu Ser Ser Glu Glu Leu Asn Tyr Arg
385             390              395                 400

Ile His Leu Lys Gly Leu Thr Gly Thr Ala Gly Lys Ile Ser Ser Ile
            405             410              415

Ser Gln Pro Gly Asn Asp Phe Ser Thr Lys Asp Gly Asp Asn Asp Lys
            420             425              430

Cys Ile Cys Lys Cys Ser Gln Met Leu Thr Gly Gly Trp Trp Phe Asp
            435             440              445

Ala Cys Gly Pro Ser Asn Leu Asn Gly Met Tyr Tyr Pro Gln Arg Gln
    450             455              460

Asn Thr Asn Lys Phe Asn Gly Ile Lys Trp Tyr Tyr Trp Lys Gly Ser
465             470              475                 480

Gly Tyr Ser Leu Lys Ala Thr Thr Met Met Ile Arg Pro Ala Asp Phe
            485             490              495
```

COMPOSITION FOR PREVENTING AND TREATING EYE DISEASES INCLUDING ANTI-ANG2 ANTIBODY

TECHNICAL FIELD

The present invention relates to a composition for preventing and treating eye diseases comprising an anti-angiopoietin-2 (Ang2) antibody or an antigen-binding fragment thereof, and more specifically relates to novel use of an anti-Ang2 antibody specifically binding to Ang2, binding to a Tie2 receptor together with Ang2, and having improved affinity, as an agent for preventing and treating eye diseases.

BACKGROUND ART

Angiogenesis is the main cause of various eye diseases that lead to millions of cases of blindness worldwide every year. In particular, representative examples of various eye diseases caused by abnormal blood vessels comprise age-related macular degeneration, diabetic retinopathy, and glaucoma.

Age-related macular degeneration is a disease that refers to the collapse or destruction of the macula occurring with the aging process, and usually occurs in people over 50 years of age. This disease is classified into a non-exudative (dry) type, wherein accumulation of small waste called "drusen" causes macular atrophy and thus loss of visual function, and an exudative (wet) type, wherein exudate escaping from abnormal new blood vessels generated due to hypoxia of the retina and choroid, and accumulation of oxidative stress leads to macular edema, and repetition of this process causes permanent degeneration in visual cells and retinal pigment epithelial cell layers (RPE cell layers) of the macula and thus loss of vision. In particular, wet-type macular degeneration has a high frequency of incidence of blindness, and the prevalence thereof in Korea is estimated to be 37 per 10,000 people. The cause of macular degeneration has not been elucidated yet, but age is a known risk factor, and other notable environmental factors comprise smoking, hypertension, obesity, genetic predispositions, excessive UV exposure, low antioxidant concentrations in the blood and the like. Currently, treatment for wet-type macular degeneration mainly focuses on antibody injection therapy for vascular endothelial growth factors, and other treatments such as laser photocoagulation, photodynamic therapy and vitrectomy are known, but there is no complete treatment yet to date.

Diabetic retinopathy is a complication of the eye involving decreased visual acuity due to retinal microcirculation disorder upon peripheral circulatory disorder due to diabetes. In early stages, diabetic retinopathy cause no symptoms or only mild vision problems, but may ultimately lead to blindness. Diabetic retinopathy can occur in anyone having Type 1 or Type 2 diabetes.

Glaucoma is a chronic optic nerve disease, more particularly, a severe refractory disease that leads to loss of vision due to progressive degeneration of optic nerves, progressive loss of retinal ganglion cells and visual field defect. Various risk factors of glaucoma comprise age, race, gender and hypertension, but intraocular pressure elevation is known to be the most important cause of various kinds of glaucoma, especially primary open-angle glaucoma. Glaucoma is considered to be due to intraocular pressure elevation resulting from increased resistance of the aqueous humor drainage pathway passing through the Schlemm's canal and trabecular meshwork. However, the molecular biological mechanism causing the problems associate with the aqueous humor drainage pathway has not been verified to date. For the treatment of glaucoma, there are methods of using drugs for reducing the production of aqueous humor or laser trabeculoplasty, surgically forming a new aqueous humor drainage pathway and the like. However, conventional non-surgical treatment is incapable of solving aqueous humor drainage pathway abnormalities and thus the effects thereof are insufficient, and surgical treatment often results in clogging of the newly formed aqueous humor drainage pathway due to the normal tissue-healing reaction. Accordingly, there is no fundamental therapeutic method yet.

Angiopoietin-2 (Ang2) is an antagonistic ligand of the receptor Tie2 present in vascular endothelial cells and functions to suppress signal transduction by Tie2 by competing for binding Tie2 with angiopoietin-1 (Ang1), which is an agonist of Tie2. Ang1, which is the ligand that activates the Tie2 receptor, acts as a major regulator to maintain stability of vessels by maintaining the barrier function of vascular endothelial cells. In overexpression of vascular endothelial growth factors or inflammation, vascular endothelial cells are activated and vascular permeability is increased. At this time, Ang1 induces stabilization of vascular endothelial cells and reduces vascular permeability by promoting junctional integrity of vascular endothelial cells, while increased Ang2 in activated vascular endothelial cells functions to inhibit stabilization of the vascular endothelial cells by competing with Ang1. Thus, Ang2 inhibit Ang1-Tie2 binding and its signal transduction which maintain the stability of vascular endothelial cells, thereby promoting angiogenesis through the dynamic rearrangement of blood vessels. Overexpression of Ang2 in various solid cancers and blood cancers has been reported, and overexpression of Ang2 in various diseases such as sepsis, bacterial infection, lung damage and kidney damage has been reported.

In the prior art, Korean Patent Laid-open No. 10-2015-0014077 identified an anti-Ang2 antibody that specifically binds to angiopoietin-2 (Ang2), which is an angiogenesis-inducing factor, additionally binds to a Tie2 receptor together with Ang2, and/or has improved humanization ability and/or affinity, the use of such anti-Ang2 antibody as an anticancer agent (Korean Patent Laid-open No. 10-2015-0032075) and the use thereof in the treatment of sepsis (Korean Patent Laid-open No. 10-2015-0028087). However, there has been no experimental evidence on the use of the anti-Ang2 antibody for the treatment of eye diseases.

Therefore, the present inventors have made efforts to develop therapeutic agents for various eye diseases caused by abnormal blood vessels. As a result, the present inventors have found that an anti-Ang2 antibody specifically binding to Ang2 and binding to a Tie2 receptor together with Ang2 is effective in inhibiting vascular leakage and choroidal angiogenesis and in improving choroidal flow in a wet-type macular degeneration animal model, is effective in alleviating vascular leakage and inhibiting macrophage infiltration in a diabetic retinopathy animal model, and is effective in enhancing Schlemm's canal homeostasis and decreasing intraocular pressure in a glaucoma model. Based on this finding, the present invention has been completed.

PRIOR ART

Korean Patent Laid-open No. 10-2015-0136031
Korean Patent Laid-open No. 10-2015-0014077
Korean Patent Laid-open No. 10-2015-0032075
Korean Patent Laid-open No. 10-2015-0028087

DISCLOSURE

Technical Problem

Therefore, it is one object of the present invention to provide novel use of an anti-Ang2 antibody and a pharmaceutical composition for preventing and treating eye diseases comprising an anti-angiopoietin-2 (Ang2) antibody or an antigen-binding fragment thereof.

It is another object of the present invention to provide a method of treating eye diseases comprising administering to a patient a pharmaceutical composition comprising an anti-angiopoietin-2 (Ang2) antibody or an antigen-binding fragment thereof and the use of the pharmaceutical composition comprising an anti-angiopoietin-2 (Ang2) antibody or an antigen-binding fragment thereof for treating or preventing eye diseases.

Technical Solution

To achieve the above objects, the present invention provides a pharmaceutical composition for preventing or treating an eye disease comprising an anti-angiopoietin-2 (Ang2) antibody or an antigen-binding fragment thereof.

The present invention also provides the pharmaceutical composition wherein the eye disease is selected from the group consisting of macular degeneration, diabetic retinopathy and glaucoma.

The present invention also provides the pharmaceutical composition wherein the glaucoma is primary open-angle glaucoma.

The present invention also provides the pharmaceutical composition wherein the anti-Ang2 antibody comprise:

a heavy-chain complementarity-determining region comprising at least one selected from the group consisting of a polypeptide comprising the amino acid sequence of SEQ ID NO: 1 (CDR-H1), a polypeptide comprising the amino acid sequence of SEQ ID NO: 2 (CDR-H2), and a polypeptide comprising the amino acid sequence of SEQ ID NO: 3 (CDR-H3), or a heavy-chain variable region comprising the at least one heavy-chain complementarity-determining region (CDR); and a light-chain complementarity-determining region comprising at least one selected from the group consisting of a polypeptide comprising the amino acid sequence of SEQ ID NO: 4 (CDR-L1), a polypeptide comprising the amino acid sequence of SEQ ID NO: 5 (CDR-L2), and a polypeptide comprising the amino acid sequence of SEQ ID NO: 6 (CDR-L3), or a light-chain variable region comprising the at least one light-chain complementarity-determining region (CDR).

The present invention also provides the pharmaceutical composition wherein the anti-Ang2 antibody may comprise:

a heavy-chain variable region comprising the amino acid sequence of SEQ ID NO: 7 and a light-chain variable region comprising the amino acid sequence of SEQ ID NO: 8.

The present invention also provides a method for preventing or treating an eye disease comprising administering to a patient a pharmaceutical composition comprising an anti-Ang2 antibody or an antigen-binding fragment thereof.

The present invention also provides a method for preventing or treating primary open-angle glaucoma comprising administering to a patient a pharmaceutical composition comprising an anti-Ang2 antibody or an antigen-binding fragment thereof.

The present invention also provides the use of a pharmaceutical composition comprising an anti-Ang2 antibody or an antigen-binding fragment thereof for the treatment or prevention of an eye disease.

The present invention also provides the use of a pharmaceutical composition comprising an anti-Ang2 antibody or an antigen-binding fragment thereof for the treatment or prevention of primary open-angle glaucoma.

DETAILED DESCRIPTION OF THE INVENTION

Figure 1:
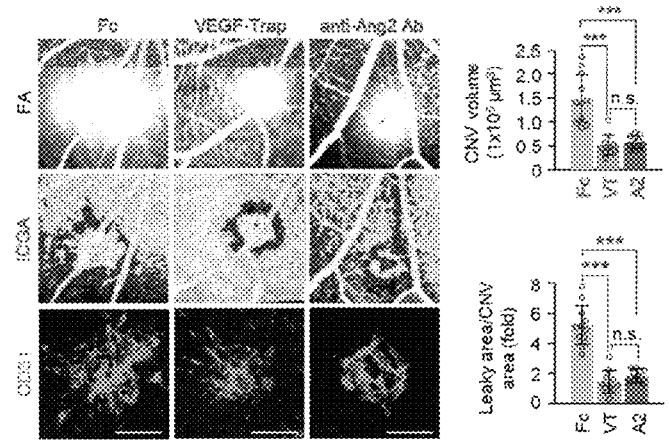
FIG. 1 shows the preventive and therapeutic effects of administration of the anti-Ang2 antibody on inhibition of vascular leakage and choroidal angiogenesis in a wet-type macular degeneration model.
Figure 1:
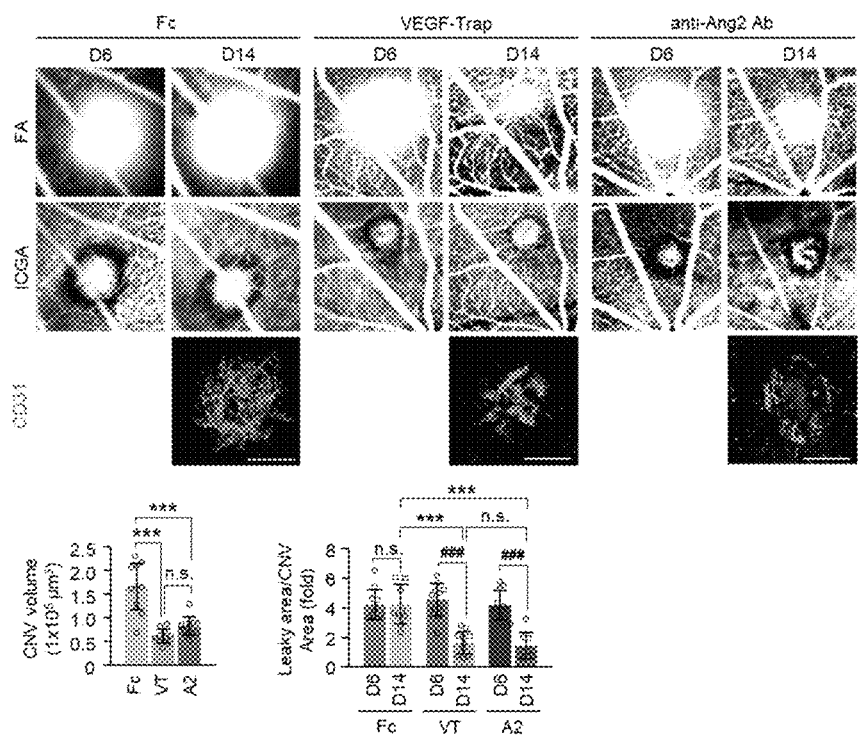

Unless defined otherwise, all the technical and scientific terms used herein have the same meanings as appreciated by those skilled in the field to which the present invention pertains. In general, the nomenclature used herein and the experimentation method described below are well-known in the art and are ordinarily used.

In one embodiment of the present invention, it is identified that an anti-Ang2 antibody or an antigen-binding fragment thereof specifically binding to Ang2 and binding to a Tie2 receptor together with Ang2 is effective in inhibiting vascular leakage and choroidal angiogenesis and improving choroidal perfusion (flow) in a macular degeneration animal model, is effective in alleviating vascular leakage and inhibiting macrophage infiltration in a diabetic retinopathy animal model, and is effective in enhancing Schlemm's canal homeostasis and decreasing intraocular pressure in a glaucoma model.

Accordingly, in one aspect, the present invention is directed to a composition for preventing or treating an eye disease comprising an anti-angiopoietin-2 (Ang2) antibody or an antigen-binding fragment thereof.

In another aspect, the present invention is directed to a method for preventing or treating an eye disease comprising administering to a patient the pharmaceutical composition comprising the anti-Ang2 antibody or an antigen-binding fragment thereof.

In another aspect, the present invention is directed to the use of a pharmaceutical composition comprising the anti-Ang2 antibody or the antigen-binding fragment thereof for the treatment or prevention of an eye disease.

The anti-Ang2 antibody of the present invention is an antibody targeting Ang2, which is an angiogenesis-inducing factor. The anti-Ang2 antibody specifically binds to Ang2 to inhibit the functions of Ang2 and thereby inhibits angiogenesis and reduce vascular density in cancer tissues. In addition, the anti-Ang2 antibody induces activation of Tie2 by binding to Tie2 together with Ang2 and thereby normalizes the blood vessels structurally and/or functionally. The anti-Ang2 antibody down-regulates Ang2 in diseases associated with abnormal activation and dysfunction of blood vessels, such as cancer, sepsis and eye diseases, and binds to a Tie2 receptor together with Ang2 to activate the Tie2 receptor, induce structural/functional normalization of blood vessels, and thereby provide an effect of treating diseases.

Specifically, the anti-Ang2 antibody of the present invention may specifically recognize Ang2 and bind to a Tie2 receptor together with Ang2. In addition, the anti-Ang2 antibody may be one that induces activation of the Tie2 receptor. The activation of such a Tie2 receptor may result in an increase in phosphorylation of the Tie2 receptor and/or phosphorylation of a protein associated with its downstream signaling pathway, for example, at least one selected from the group consisting of Akt (NM_005163), eNOS (NM_000603), 42/44 (NM_002745) and the like. In addition, the anti-Ang2 antibody may induce internalization of the Tie2 receptor into cells. In other words, unlike conventional anti-Ang2 antibodies, the anti-Ang2 antibody may specifically bind to Ang2, may not inhibit binding between Ang2 and Tie2 receptor, and may bind to the Tie2 receptor with Ang2 to form a complex and induce activation of the Tie2 receptor.

In the present invention, the Ang2 protein, which acts as an antigen of an anti-Ang2 antibody, is closely related to angiogenesis, is a soluble ligand present in the blood and is widely applied to angiogenesis, metastasis, invasion of cancer cells and the like. The Ang2 may be derived from a mammal such as a primate such as a human or a monkey, or a rodent such as a mouse or a rat. Examples of the Ang2 include, but are not limited to, human Ang2 (such as NCBI Accession No. 015123), monkey Ang2 (such as NCBI Accession No. Q8MIK6), mouse Ang2 (such as NCBI Accession No. 035608), rat Ang2 (such as NCBI Accession No. 035462) and the like.

The Tie2 receptor (TEK tyrosine kinase) of the present invention is an Ang1 receptor and is expressed in endothelial cells of various mammals such as mice (NM_013690; NP_038718), rats and humans (NM_000459; NP_000450) and is involved in various downstream signaling.

The anti-Ang2 antibody of the present invention, which binds specifically to Ang2, but does not inhibit binding between Ang2 and Tie2 receptor, and forms a complex (antibody/Ang2/Tie2) with Ang2 and Tie2 receptors, has a feature of inducing dimerization of the antibody and has a feature of being capable of inducing activation of the Tie2 receptor and downstream signaling thereof by effectively clustering the Tie2 receptor complexed therewith. Based on this mechanism, the antibody of the present invention has dual functions, including binding to Ang2 to induce intracellular movement and degradation, to thereby function to inhibit the functions of Ang2 and lower the level of circulating Ang2, as well as binding to a Tie2 receptor together with the Ang2, to activate the Tie2 receptor, like Ang1, and thereby induce stabilization of vascular endothelial cells. For this reason, the antibody of the present invention is useful in the treatment of diseases caused by Ang2 overexpression as well as diseases caused by deteriorated stability of vascular endothelial cells which is caused by increased vascular permeability.

The anti-Ang2 antibody may recognize, as an epitope, all or part (for example, one or more amino acid residues selected from the group consisting of amino acid residue regions that are exposed to the outside of loop 1 in SEQ ID NO: 9) of loop 1 (the site ranging from the amino acid at position 417~434 in SEQ ID NO: 9) of human Ang2 (hAng2; SEQ ID NO: 9; Accession #015123) or an amino acid sequence site comprising 2 to 20, 2 to 15, 2 to 10, or 2 to 5 consecutive or non-consecutive amino acids comprising one or more amino acid residues that are exposed to the outside of loop 1 in SEQ ID NO: 9, or may specifically bind to this site. The following Table 1 shows the Ang2 sequence of SEQ ID NO: 9.

TABLE 1

| Ang2 sequence (SEQ ID NO: 9) |
|---|
| MWQIVFFTLS CDLVLAAAYN NFRKSMDSIG KKQYQVQHGS |
| CSYTFLLPEM DNCRSSSSPY VSNAVQRDAP LEYDDSVQRL |
| QVLENIMENN TQWLMKLENY IQDNMKKEMV EIQQNAVQNQ |
| TAVMIEIGTN LLNQTAEQTR KLTDVEAQVL NQTTRLELQL |
| LEHSLSTNKL EKQILDQTSE INKLQDKNSF LEKKVLAMED |
| KHIIQLQSIK EEKDQLQVLV SKQNSIIEEL EKKIVTATVN |
| NSVLQKQQHD LMETVNNLLT MMSTSNSAKD PTVAKEEQIS |
| FRDCAEVFKS GHTTNGIYTL TFPNSTEEIK AYCDMEAGGG |
| GWTIIQRRED GSVDFQRTWK EYKVGFGNPS GEYWLGNEFV |
| SQLTNQQRYV LKIHLKDWEG NEAYSLYEHF YLSSEELNYR |
| IHLKGLTGTA GKISSISQPG NDFSTKDGDN DKCICKCSQM |
| LTGGWWFDAC GPSNLNGMYY PQRQNTNKFN GIKWYYWKGS |
| GYSLKATTMM IRPADF |

The anti-Ang2 antibody may recognize, as an epitope, Q418 or P419 located in loop 1 of SEQ ID NO: 9, or a combination of Q418 and P419, or an amino acid sequence site comprising 2 to 20, 2 to 15, 2 to 10, or 2 to 5 consecutive or non-consecutive amino acids comprising an amino acid residue of Q418 or P419 in SEQ ID NO: 9 or a combination of Q418 and P419, or may specifically bind to this site. Preferably, the anti-Ang2 antibody may recognize amino acid residues of Q418 and P419 of SEQ ID NO: 9 as an epitope, or may specifically bind to these sites.

Q418, P419, or an amino acid site comprising the same, to which the anti-Ang2 antibody specifically binds, is an exposed amino acid residue located in loop 1 of the three-dimensional structure of Ang2, and is considered to be directly involved in binding between Ang2 and Tie2 receptors or regulate the same. In the Q418, P419, or an amino acid site comprising the same, to which the anti-Ang2 antibody specifically binds, the term "non-continuous amino acids" may mean amino acids that are adjacent to one another in the two- or three-dimensional structure of a protein, but are not continuous in the amino acid sequence. Thus, as used herein, the term "continuous or non-continuous amino acid residue" may refer to a continuous amino acid residue in the one, two or three-dimensional structure of proteins.

The anti-Ang2 antibody comprises not only a complete antibody, but also an antigen-binding fragment of the antibody molecule.

The complete antibody has a structure having two full-length light chains and two full-length heavy chains, wherein each light chain is linked to the corresponding heavy chain by a disulfide bond. The heavy chain constant region has gamma (γ), mu (μ), alpha (α), delta (δ) and epsilon (ε) types and is subclassified into gamma 1 (γ1), gamma 2 (γ2), gamma 3 (γ3), gamma 4 (γ4), alpha 1 (α1) and alpha 2 (α2). The constant region of the light chain has kappa (κ) and lambda (λ) types. The basic four-chain antibody unit is a heterotetramer glycoprotein consisting of two identical light chains (L) and two identical heavy chains (H). The light chain has a variable region (VL) at the N-terminus and a constant region at another terminus. The heavy chain has a variable region (VH) at the N-terminus and three constant regions (CH) for α and γ chains, and four CH regions for μ and ε isoforms. The term "variable" means that a particular portion of the variable region is significantly different in sequence between antibodies. The V region mediates antigen binding and defines the specificity of a particular antibody for a particular antigen thereof. Variability is concentrated in three segments called "hypervariable region (HVR)", that is, CDR, in both light- and heavy-chain variable regions. The more highly conserved portion of the variable region is called a "framework region (FR)". The heavy and light-chain variable regions have FR1, CDR1, FR2, CDR2, FR3, CDR3 and FR4 structures from the N-terminus to the C-terminus.

As used herein, the term "heavy chain" encompasses both a full-length heavy chain, which comprises a variable domain (VH) comprising an amino acid sequence having a sufficient variable region sequence for imparting specificity to an antigen and three constant domains (CH1, CH2 and CH3), and a fragment thereof.

As used herein, the term "light chain" encompasses both a full-length light chain, which comprises a variable domain (VL) comprising an amino acid sequence having a sufficient variable region sequence for imparting specificity to an antigen and a constant domain (CL), and a fragment thereof.

The term "antigen-binding fragment of antigen" or "antibody fragment" as used herein refers to a fragment that has antigen-binding ability and comprises Fab, F(ab'), Fv or the like.

The "Fv" fragment is an antibody fragment comprising complete antibody recognition and binding sites. Such a region comprise a dimer, for example, scFv, that consists of one heavy-chain variable domain and one light-chain variable domain substantially tightly covalently connected to each other.

A "Fab" fragment comprises variable and constant domains of the light chain and a variable domain and a first constant domain (CH1) of the heavy chain. A F(ab')₂ antibody fragment generally comprises a pair of Fab fragments covalently linked via a hinge cysteine located there between near the carboxyl end thereof.

The "single chain Fv" or "scFv" antibody fragment comprises VH and VL domains of the antibody, wherein these domains are present in a single polypeptide chain. The Fv polypeptide may further comprise a polypeptide linker between the VH domain and the VL domain in order for the scFv to form a target structure for antigen binding.

In the present invention, the anti-Ang2 antibody may comprise:

a heavy-chain complementarity-determining region (CDR) comprising at least one selected from the group consisting of a polypeptide comprising the amino acid sequence of SEQ ID NO: 1 (CDR-H1), a polypeptide comprising the amino acid sequence of SEQ ID NO: 2 (CDR-H2), and a polypeptide comprising the amino acid sequence of SEQ ID NO: 3 (CDR-H3), or a heavy-chain variable region comprising the heavy-chain complementarity-determining region (CDR);

a light-chain complementarity-determining region (CDR) comprising at least one selected from the group consisting of a polypeptide comprising the amino acid sequence of SEQ ID NO: 4 (CDR-L1), a polypeptide comprising the amino acid sequence of SEQ ID NO: 5 (CDR-L2), and a polypeptide comprising the amino acid sequence of SEQ ID NO: 6 (CDR-L3), or a light-chain variable region comprising the light-chain complementarity-determining region (CDR); or a combination of the at least one heavy-chain complementarity-determining region and the at least one light-chain complementarity-determining region; or a combination of the heavy-chain variable region and the light-chain variable region.

Preferably, the anti-Ang2 antibody may comprise:

a heavy-chain complementarity-determining region (CDR) comprising a polypeptide comprising the amino acid sequence of SEQ ID NO: 1 (CDR-H1), a polypeptide comprising the amino acid sequence of SEQ ID NO: 2 (CDR-H2), and a polypeptide comprising the amino acid sequence of SEQ ID NO: 3 (CDR-H3), or a heavy-chain variable region comprising the heavy-chain complementarity-determining region; and a light-chain complementarity-determining region (CDR) comprising a polypeptide comprising the amino acid sequence of SEQ ID NO: 4 (CDR-L1), a polypeptide comprising the amino acid sequence of SEQ ID NO: 5 (CDR-L2), and a polypeptide comprising the amino acid sequence of SEQ ID NO: 6 (CDR-L3), or a light-chain variable region comprising the light-chain complementarity-determining region.

Specifically, the heavy-chain complementarity-determining region and light-chain complementarity-determining region of the anti-Ang2 antibody may have the amino acid sequence set forth in the following Table 2:

TABLE 2

| Heavy chain CDR amino acid sequence | | |
|---|---|---|
| CDRH1-KABAT | CDRH2-KABAT | CDRH3-KABAT |
| SDYAWN (SEQ ID NO: 1) | KISYSGKTDYNPSLKS (SEQ ID NO: 2) | GNFEGAMDY (SEQ ID NO: 3) |
| Light chain CDR amino acid sequence | | |
| CDRL1-KABAT | CDRL2-KABAT | CDRL3-KABAT |
| KASQSVSNDVH (SEQ ID NO: 4) | YASIPYP (SEQ ID NO: 5) | QQDYSSPWT (SEQ ID NO: 6) |

In one embodiment, the heavy-chain variable region of the antibody may comprise the amino acid sequence of SEQ ID NO: 7 in the following Table 3, and the light chain of the antibody may comprise the amino acid sequence of SEQ ID NO: 8 in the following Table 3.

TABLE 3

QVQLQESGPGLVKPSETLSLTCAVSGYSITSDYAWNWIRQPPGKGLE
WMGKISYSGKTDYNPSLKSRSTISRDTSKNQFSLKLSSVTAADTAVY
YCARGNFEGAMDYWGQGTLVTVSS (SEQ ID NO: 7)

DIQMTQSPSSLSASVGDRVTITCKASQSVSNDVHWYQQKPGKAPKLL
IYYASIPYPGVPSRFSGSGSGTDFTLTISSLQPEDFATYYC**QQDYSS
PWT**FGQGTKLEIK (SEQ ID NO: 8)

(In SEQ ID NO: 7, underlined bold letters represent CDRH1, CDRH2 and CDRH3 in this order)
(In SEQ ID NO: 8, underlined bold letters represent CDRL1, CDRL2, CDRL3 in this order)

Accordingly, the anti-Ang2 antibody may comprise a heavy-chain variable region comprising the amino acid sequence of SEQ ID NO: 7, a light-chain variable region comprising the amino acid sequence of SEQ ID NO: 8, or a combination of the heavy-chain variable region and the light-chain variable region. For example, the anti-Ang2 antibody may comprise a heavy-chain variable region comprising the amino acid sequence of SEQ ID NO: 7 and a light-chain variable region comprising the amino acid sequence of SEQ ID NO: 8.

In the present invention, the antibody comprises both an animal-derived antibody, a chimeric antibody, a humanized antibody and a human antibody. The animal-derived antibody that is produced by immunizing an animal in need of immunization with a desired antigen may generally cause immune rejection when administered to a human for therapeutic purposes. In an attempt to suppress such immune rejection, a chimeric antibody has been developed. The chimeric antibody is obtained by substituting the constant region of the animal-derived antibody causing the anti-isotype reaction with the constant region of the human antibody through a genetic engineering method. The chimeric antibody has significantly improved anti-isotype reactions compared to the animal-derived antibody, but still comprises animal-derived amino acids in the variable region and thus has potential side effects on anti-isotype reactions. In an attempt to suppress such side effects, a humanized antibody has been developed. The humanized antibody is produced by grafting the complementarity-determining region (CDR) site, which plays a key role in the binding of an antigen in the variable region of the chimeric antibody to the human antibody framework.

The most important factor in CDR grafting techniques for producing humanized antibodies is to select the optimized human antibody that can best accommodate the CDR site of the animal-derived antibody. For this purpose, the use of an antibody database, the analysis of crystal structure, molecular modeling techniques and the like are utilized. However, even if the CDR site of the animal-derived antibody is grafted to the optimized human antibody framework, there may be present amino acids that affect the antigen binding while being located in the framework of the animal-derived antibody. For this reason, in many cases, antigen-binding ability is not retained. Thus, it is essential to apply additional antibody engineering techniques to restore antigen-binding ability.

According to one embodiment, the antibody may be a mouse-derived antibody, a mouse-human chimeric antibody, a humanized antibody or a human antibody.

The anti-Ang2 antibody or antigen-binding fragment thereof of the present invention has a function of inhibiting abnormal angiogenesis by inhibiting the functions of Ang2, and thus is useful for the prevention and/or treatment of eye diseases accompanied by vascular abnormalities such as macular degeneration, diabetic retinopathy and glaucoma.

The term "prevention" means any action that inhibits eye diseases or delays the progress of the same by administration of the composition according to the present invention. The term "treatment" means suppression, alleviation or removal of the progress of eye diseases.

As used herein, the term "macular degeneration" refers to a condition in which a newly formed blood vessel grows abnormally, thus causing damage to the macula and affecting vision. Macular degeneration occurs mainly in adults over 50 years of age and is divided into a non-exudative (dry) type and an exudative (wet) type. In particular, exudative (wet) macular degeneration may cause blindness, and the cause thereof has not been clearly found, but age is known to be a risk factor. Environmental factors comprise smoking, hypertension, obesity, genetic predispositions, excessive UV exposure, low antioxidant concentration in the blood, and the like.

As used herein, the term "diabetic retinopathy" refers to a complication of the eye involving decreased visual acuity due to retinal microcirculation disorder upon peripheral circulatory disorder due to diabetes. In early stages, diabetic retinopathy may cause no symptoms or only mild vision problems, but ultimately it may lead to blindness. Diabetic retinopathy can occur in anyone having Type 1 or Type 2 diabetes.

As use herein, the term "glaucoma" is a chronic optic nerve disease, more particularly, a severe refractory disease causing loss of vision due to progressive degeneration of optic nerves, progressive loss of retinal ganglionic cells, and visual field defect. Risk factors of glaucoma comprise age, race, gender and hypertension, but intraocular pressure elevation is known to be the most important cause of various kinds of glaucoma, especially primary open-angle glaucoma. Thus, the present invention can be used for the prevention and/or treatment of primary open-angle glaucoma.

The pharmaceutical composition according to the present invention may further comprise a pharmaceutically acceptable carrier, and the carrier may be one that is commonly used for the preparation of drugs, and may comprise at least one selected from the group consisting of lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, but is not limited thereto. Also, the pharmaceutical composition may further comprise at least one selected from the group consisting of a diluent, an excipient, a lubricant, a wetting agent, a sweetening agent, a flavoring agent, an emulsifying agent, a suspending agent and a preservative.

A pharmaceutically effective amount of the pharmaceutical composition or the antibody may be administered orally or parenterally. For parenteral administration, the pharmaceutical composition or the antibody may be administered through intravenous injection, subcutaneous injection, intramuscular injection, intraperitoneal injection, endothelial administration, topical administration, intranasal administration, intrapulmonary administration, intrarectal administration and the like. Upon oral administration, proteins or peptides are digested, so that an oral composition may be coated with an active agent or formulated so as to protect the same from being degraded in the stomach. In addition, the composition may be administered using any device capable of transferring the active substance to target cells.

The content of the anti-Ang2 antibody in the pharmaceutical composition may vary depending on factors such as formulation method, administration method, and age, body weight, gender, pathological conditions, diet, administration time, administration interval, administration route, excretion rate and responsiveness of the patient. For example, the daily dose of the anti-Ang2 antibody may be within the range of 0.001 to 1,000 mg/kg, specifically 0.01 to 100 mg/kg, and more specifically 0.1 to 50 mg/kg, but is not limited thereto. The daily dose may be prepared by formulation into a single dosage form with a unit dose, formulation in an appropriate amount, or intrusion into a multi-dose container. The pharmaceutically effective amount may mean the content or dose of the active ingredient that can exhibit the desired pharmacological effect, and may vary depending on the formulation method, the administration method, and the age, body weight, gender, pathological conditions, diet, administration time, administration interval, administration route, excretion rate and responsiveness of the patient.

The pharmaceutical composition may be in the form of a solution, a suspension, a syrup or an emulsion in an oil or aqueous medium, or may be formulated in the form of an extract, a powder, a granule, a tablet or a capsule. The pharmaceutical composition may further comprise a dispersant or a stabilizer.

In particular, the pharmaceutical composition comprising the anti-Ang2 antibody or an antigen-binding fragment thereof can be formulated into immunoliposome, since the pharmaceutical composition comprises the antibody. A liposome containing an antibody can be prepared according to a method well-known in the art. The immunoliposome is a lipid composition comprising phosphatidylcholine, cholesterol and polyethylene glycol-derivatized phosphatidylethanolamine, and can be prepared through reverse phase evaporation. For example, the Fab' fragment of an antibody can be conjugated to a liposome via a disulfide exchange reaction.

Hereinafter, the present invention will be described in more detail with reference to examples. However, it will be obvious to those skilled in the art that these examples are suggested only for illustration of the present invention and should not be construed as limiting the scope of the present invention.

Example 1: Effect of Anti-Ang2 Antibody in Macular Degeneration Model

1. Production of Wet-Type Macular Degeneration Model

In order to produce a wet-type macular degeneration model, the pupil of an 8-weeks-old mouse was dilated by dropping an iridodilator thereto and then a laser was radiated at four positions in each mouse eye while observing the retina using a slit lamp microscope to induce lesions. At this time, only the lesions where the Bruch's membrane was found to be ruptured were used for analysis, and the cases in which bleeding was induced were excluded from the analysis.

2. Effects of Inhibition of Vascular Leakage and Choroidal Angiogenesis

In order to identify whether the anti-Ang2 antibody including the heavy-chain CDRs of SEQ ID NOS: 1 to 3 and light-chain CDRs of SEQ ID NOS: 4 to 6 set forth in Table 2 was effective in inhibiting vascular leakage and choroidal angiogenesis, the evaluation was performed in two sections, that is, prevention and treatment sections. In order to compare the therapeutic efficacy between the anti-Ang2 antibody and the anti-vascular endothelial growth factor antibody, which is the most widely used drug, an experiment was performed on three groups in total (placebo group, anti-Ang2-antibody-administered group and anti-vascular-endothelial-growth-factor-administered group).

As a result, in both the prevention and treatment sections, the anti-Ang2-antibody-administered group had a considerable decrease in vascular leakage (prevention: 63.1%; treatment: 66.4%) and choroidal angiogenesis volume (prevention: 61.3%, treatment: 50.1%), compared to the placebo group. The anti-Ang2-antibody-administered group exhibited similar degrees of vascular leakage inhibition and angiogenesis volume decrease, compared to the group administered with the anti-vascular endothelial cell growth factor antibody (FIG. 1).

3. Effect of Improvement of Choroidal Flow

Treatment with the anti-vascular endothelial growth factor, which has been widely used for the treatment of wet-type macular degeneration, temporarily reduces the volume of choroidal angiogenesis and inhibits vascular leakage. For this reason, treatment with anti-vascular endothelial growth factor has a drawback in that it is necessary to periodically perform repeated injections over a long period of time, and has side effects of inducing retraction of choroidal capillary blood vessels, thus worsening retinal and choroidal hypoxia and oxidative stress, and having a limitation of high frequency of recurrence of choroidal angiogenesis. In addition, treatment with anti-vascular endothelial growth factor has fatal limitations of inducing degeneration of the retinal pigment epithelium and optic nerve cells, thus causing permanent loss of vision.

Figure 2:
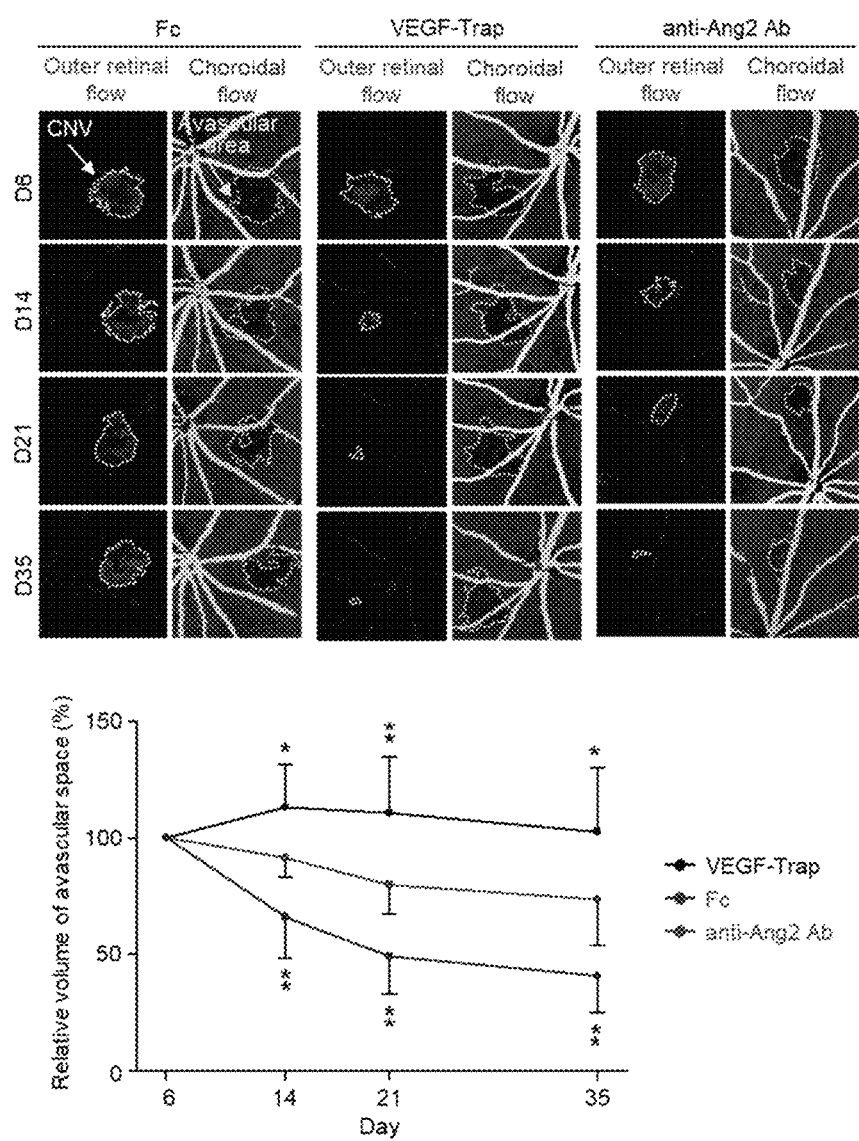
FIG. 2 shows the effects of administration of the anti-Ang2 antibody on improvement of choroidal perfusion (flow) in the wet-type macular degeneration model.

In order to identify whether or not the anti-Ang2 antibody is capable of overcoming these limitations, angiography using optical coherence tomography was performed in a time series. As a result, in the group administered with the anti-vascular endothelial cell growth factor antibody, the size of the avascular choroid of the periphery of the laser-induced choroidal angiogenesis gradually increased (35.9%, 28.3% and 47.5%) during the observation period, while in the anti-Ang2-antibody-administered group, the size thereof gradually decreased (27.3%, 43.1% and 45.5%) (FIG. 2).

Therefore, the anti-Ang2 antibody exhibited similar inhibitory effects on vascular leakage and choroidal angiogenesis compared to conventional treatment with an anti-vascular endothelial growth factor. Thus it has an immediate therapeutic effect in the acute phase and reduces the size of an avascular choroidal area, thereby reducing hypoxia and oxidative stress, fundamentally inhibiting the recurrence of choroidal angiogenesis and avoiding side effects such as degeneration of retinal pigment epithelium cells and optic nerve cells.

Example 2: Effect of Anti-Ang2 Antibody in Diabetic Retinopathy Model

1. Production of Diabetic Retinopathy Model

The blood vessel changes first occurring in diabetic retinopathy are known to be hypertrophy of the retinal capillary basement membrane and the loss of perivascular cells. As these changes occur and over time, a wide range of capillary non-perfusion occurs, resulting in excessive formation of vascular endothelial growth factors from the ischemic retina and leading to retinal angiogenesis that causes complications such as bleeding and inflammation. A new diabetic retinopathy model was constructed in mice, based on the consideration that the loss of perivascular cells occurs as an initial change of diabetic retinopathy and excessively produced vascular endothelial growth factor is important for the progression of diabetic retinopathy.

Figure 3:
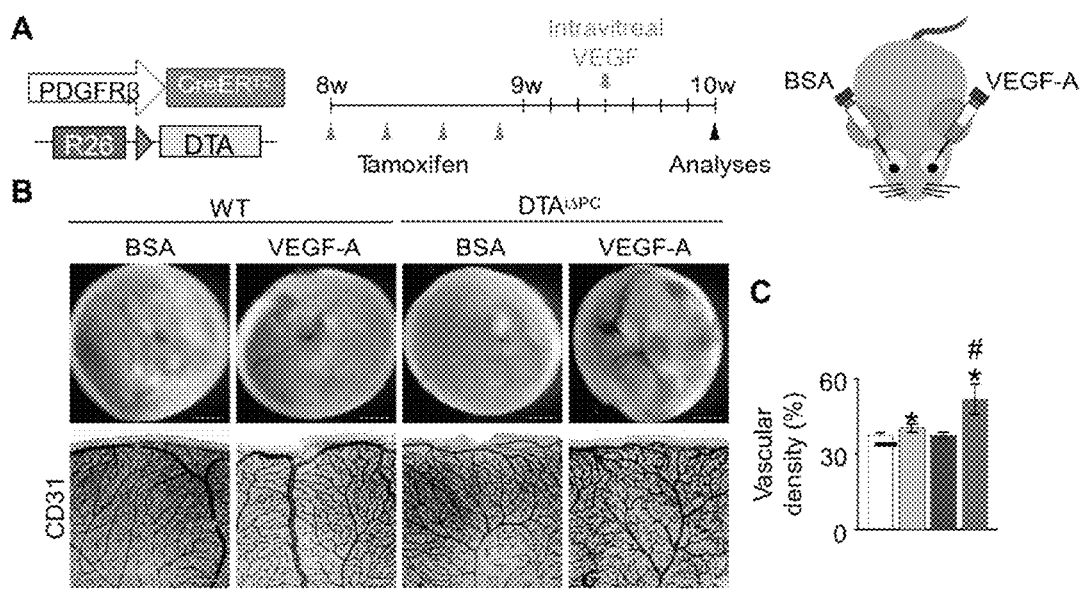
FIG. 3 shows the process for establishment and verification of a diabetic retinopathy model. Specifically, the diabetic retinopathy model is established by injection of vascular endothelial growth factors (VEGF-A) and loss of perivascular cells (DTAiAPC) (A) and it is observed that blood leakage is significantly increased in the established diabetic retinopathy model mouse (B-C).

First, using genetically engineered mice, all cells expressing the platelet-derived growth factor receptor (PDGF-receptor-beta), which is known to be expressed specifically in perivascular cells were killed by a diphtheria toxin which was produced by externally injected tamoxifen. When injecting the vascular endothelial growth factor into the eye of the genetically engineered mouse and comparing the same with the retina of the eye of the control group, a significant increase in vascular leakage was observed in the genetically engineered mouse (FIG. 3). According to above process, an animal model, based on the development mechanism of diabetic retinopathy and having a vascular disease similar to diabetic retinopathy, was constructed.

Figure 4:
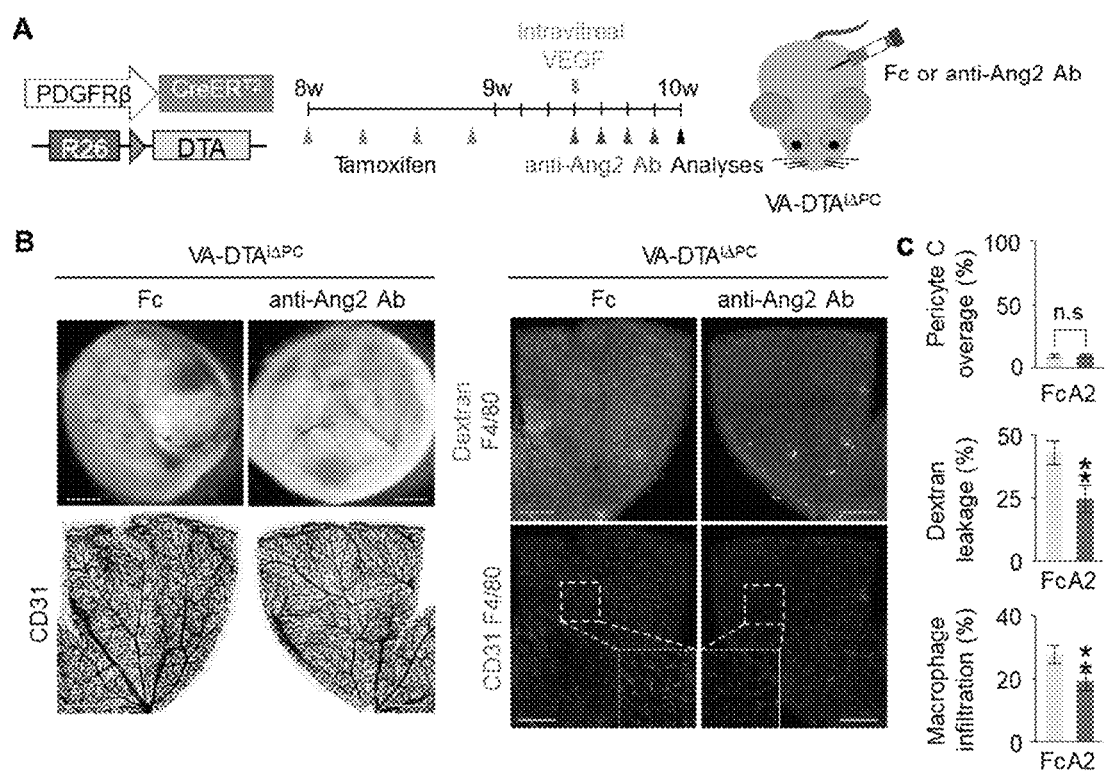
FIG. 4 shows the effect of the anti-Ang2 antibody on alleviation of vascular leakage and inhibition of macrophage infiltration in a diabetic retinopathy model.

2. Effects of Alleviation of Vascular Leakage and Inhibition of Macrophage Infiltration Diabetic retinopathy model mice showed vascular leakage and macrophage infiltration. Intraperitoneal administration of the anti-Ang2 antibody including the heavy-chain CDRs of SEQ ID NOS: 1 to 3 and the light-chain CDRs of SEQ ID NOS: 4 to 6 set forth in Table 2 to the diabetic retinopathy model mice resulted in reduction of visible leakage of the blood in the retina and dextran leakage in blood vessels and a decrease in macrophage infiltration (FIG. 4).

Example 3: Effect of Anti-Ang2 Antibody in Glaucoma Model

1. Production of Glaucoma Model

Figure 5:
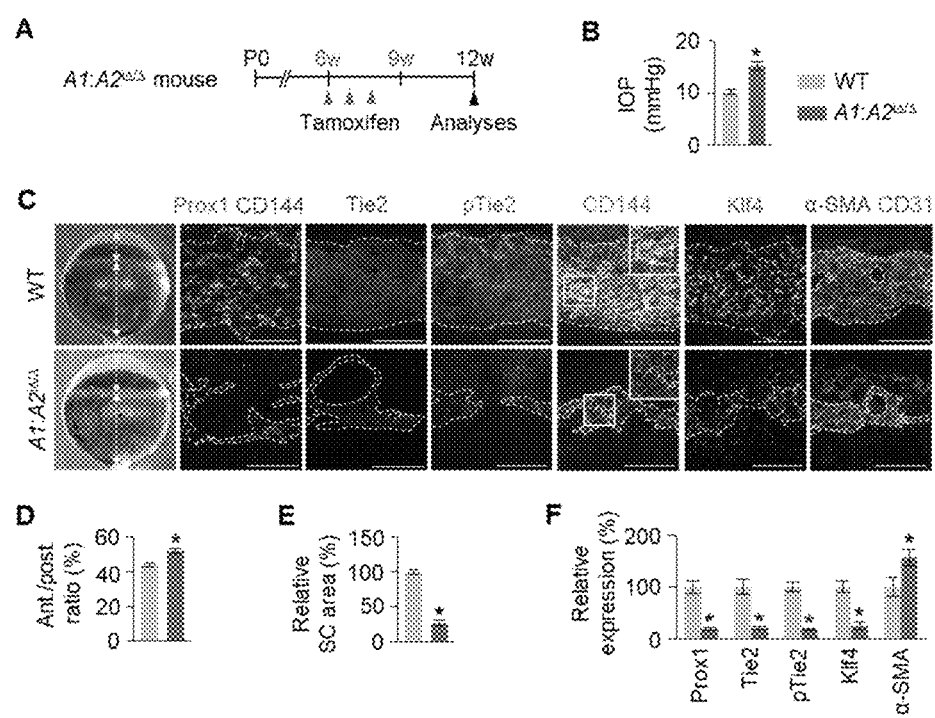
FIG. 5 shows the process for establishment and verification of a glaucoma model. Specifically, the glaucoma model inhibiting an Ang-Tie2 signal is established (A) and the formation of the Schlemm's canal and the maintenance of homeostasis are suppressed and the intraocular pressure is thus significantly elevated in the constructed glaucoma model mouse.

It is known that glaucoma is caused by increased intraocular pressure, resulting from increased resistance of the aqueous humor drainage pathway passing through the Schlemm's canal and trabecular meshwork in the eye. A glaucoma model mouse (ubiquitin-Cre, Ang1 & Ang2 double-floxed mouse) which inhibits the Ang-Tie2 signal by entirely inhibiting the expression of Ang1 and Ang2, was constructed, based on the fact that the Ang-Tie2 signal regulates the generation and regeneration of blood vessels. It was found that the constructed glaucoma model mouse significantly inhibited the formation of the Schlemm's canal and the maintenance of homeostasis thereof, and thus the intraocular pressure was significantly elevated (FIG. 5).

2. Effects of Improvement of Schlemm's Canal Homeostasis and Decrease of Intraocular Pressure After an anti-Ang2 antibody including the heavy-chain CDRs of SEQ ID Nos. 1 to 3 and the light-chain CDRs of SEQ ID Nos. 4 to 6 set forth in Table 2 was intravitreally injected into glaucoma model mice and wild-type mice with recombinant Ang2, changes in intraocular pressure, the area of the Schlemm's canal, and expression of the transcription factor Prox1 and Tie2 receptor were compared.

Figure 6:
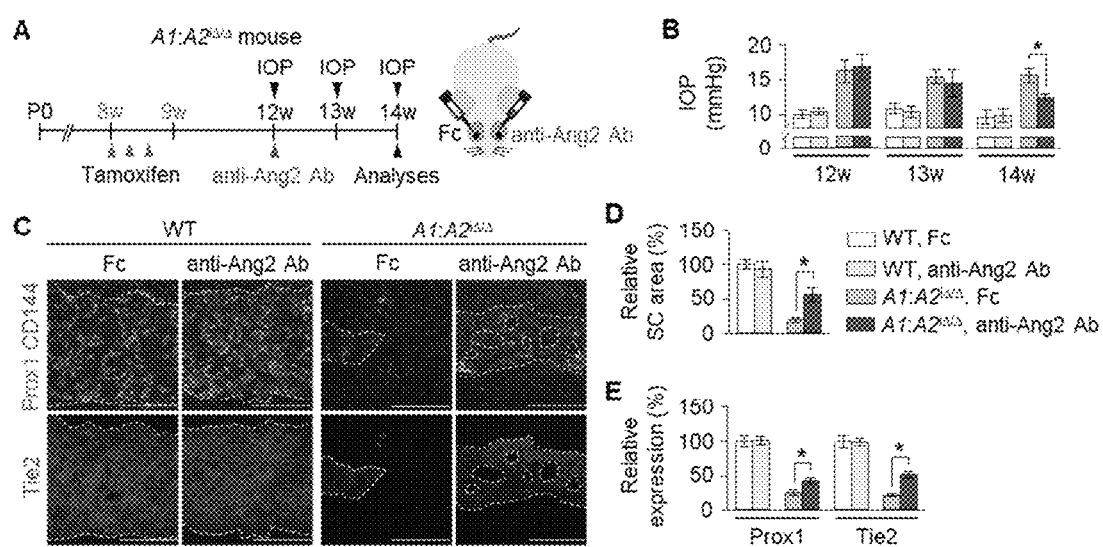
FIG. 6 shows the effects of the anti-Ang2 antibody on improvement of Schlemm's canal homeostasis and reduction of intraocular pressure in a glaucoma model.

As a result, no significant change was observed in wild-type mice even after anti-Ang2 antibody injection. In contrast, in the glaucoma model mice, a significant intraocular pressure decrease effect was observed, the area of the Schlemm's canal was significantly increased, and the expression of Prox1 and Tie2 was also increased (FIG. 6).

INDUSTRIAL AVAILABILITY

The present invention provides the therapeutic use for eye diseases of an anti-Ang2 antibody that activates a Tie2 receptor to promote downstream signal transduction, while inhibiting Ang2, thus being useful for the development of therapeutic drugs pertaining to the anti-Ang2 antibody for macular degeneration, diabetic retinopathy and glaucoma.

SEQUENCE LISTING FREE TEXT

An electronic file is attached.

The invention claimed is:

1. A method of treating primary open-angle glaucoma comprising
administering a pharmaceutical composition comprising an anti-angiopoietin-2 (Ang2) antibody or an antigen-binding fragment thereof to a patient,
wherein the anti-Ang2 antibody comprises:
a heavy-chain complementarity-determining region (CDR) comprising the amino acid sequence of SEQ ID NO: 1 (CDR-H1), the amino acid sequence of SEQ ID NO: 2 (CDR-H2), and the amino acid sequence of SEQ ID NO: 3 (CDR-H3); and
a light-chain complementarity-determining region comprising the amino acid sequence of SEQ ID NO: 4 (CDR-L1), the amino acid sequence of SEQ ID NO: 5 (CDR-L2), and the amino acid sequence of SEQ ID NO: 6 (CDR-L3).

2. The method according to claim 1, wherein the anti-Ang2 antibody comprises a heavy-chain variable region comprising the amino acid sequence of SEQ ID NO: 7 and a light-chain variable region comprising the amino acid sequence of SEQ ID NO: 8.

* * * * *